US00PP29133P2

(12) United States Plant Patent
Stemkens

(10) Patent No.: US PP29,133 P2
(45) Date of Patent: Mar. 20, 2018

(54) ***VERBENA* PLANT NAMED 'VEAZ0038'**

(50) Latin Name: *Verbena hybrida*
Varietal Denomination: VEAZ0038

(71) Applicant: SYNGENTA PARTICIPATIONS AG, Basel (CH)

(72) Inventor: Henricus Godefridus Wilhelmus Stemkens, Andijk (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/530,004

(22) Filed: Nov. 16, 2016

(51) Int. Cl.
*A01H 5/02* (2006.01)

(52) U.S. Cl.
USPC ..... Plt./308

(58) Field of Classification Search
USPC ..... Plt./308
See application file for complete search history.

*Primary Examiner* — Annette H Para
(74) *Attorney, Agent, or Firm* — Dale Skalla

(57) ABSTRACT

A new *Verbena* plant named 'VEAZ0038' particularly distinguished by medium sized inflorescences, dark velvet purple flowers, medium green, undivided leaves and a trailing plant habit

1 Drawing Sheet

Latin name of the genus and species of the plant claimed: *Verbena hybrida.*

Varietal denomination: 'VEAZ0038'.

BACKGROUND OF THE NEW PLANT

The present invention comprises a new *Verbena*, botanically known as *Verbena hybrida*, and hereinafter referred to by the variety name 'VEAZ0038'.

'VEAZ0038' is a product of a planned breeding program. The new cultivar has medium sized inflorescences, dark velvet purple flowers, medium green, undivided leaves, and a trailing plant habit.

'VEAZ0038' originated from an open pollination made in July 2012 in a greenhouse in Enkhuizen, The Netherlands. The female parent was an unpatented proprietary plant designated 'M0645-1', having a deep purple flower color, and a semi-upright plant habit.

The male parent of 'VEAZ0038' is an unpatented proprietary plant designated '2144-3', having a violet-purple flower color, huge flowers and a trailing plant habit.

The resulting seed was sown in February 2013 in a greenhouse in Enkhuizen, The Netherlands and 'VEAZ0038' was selected as one flowering plant within the progeny of the stated cross in May 2013.

The first act of asexual reproduction of 'VEAZ0038' was accomplished when vegetative cuttings were propagated from the initial selection in June 2013 in a greenhouse in Enkhuizen, The Netherlands.

BRIEF SUMMARY OF INVENTION

Horticultural examination of plants grown from cuttings of the plant initiated in the fall of 2013, and continuing thereafter, has demonstrated that the combination of characteristics as herein disclosed for 'VEAZ0038' are firmly fixed and are retained through successive generations of asexual reproduction.

'VEAZ0038' has not been observed under all possible environmental conditions. The phenotype may vary significantly with variations in environment such as temperature, light intensity, and day length.

'VEAZ0038' has not been made publicly available prior to the effective filing date of this application, notwithstanding any disclosure that may have been made less than one year prior to the effective filing date of this application by the inventor or another who obtained 'VEAZ0038' directly from the inventor.

The following traits have been repeatedly observed and are determined to be basic characteristics of the new variety. The combination of these characteristics distinguishes this *Verbena* as a new and distinct variety.

BRIEF DESCRIPTION OF THE PHOTOGRAPHS

The accompanying photographic drawings show typical flower and foliage characteristics of 'VEAZ0038' with colors being as true as possible with an illustration of this type.

Figure 1:
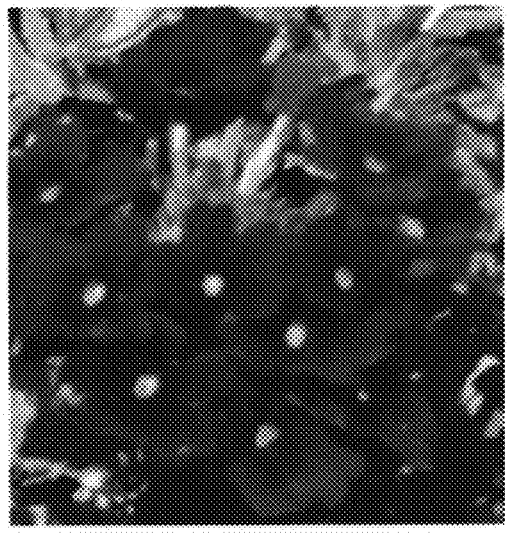
Figure 2:
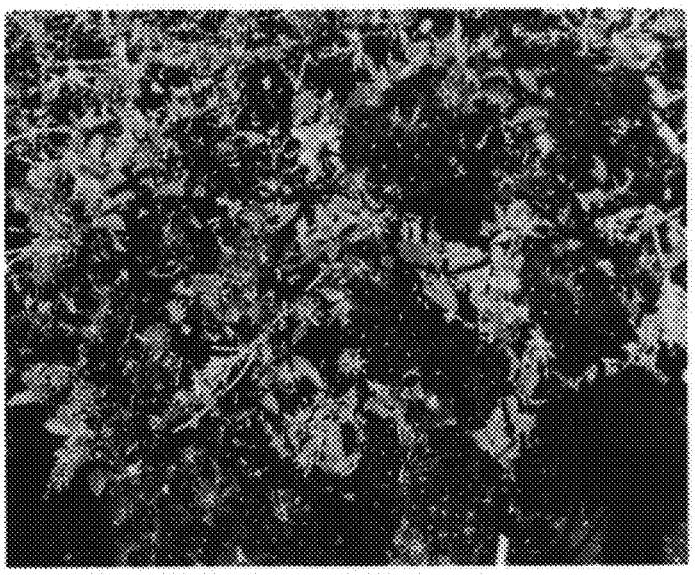

The photographic drawing in FIG. 1 shows a close view of an inflorescence of the new plant and in FIG. 2 a whole flowering plant. The aforementioned photographs were taken in late September 2016 in Andijk, The Netherlands. The plants were about 22 weeks old and were grown in hanging baskets.

DETAILED BOTANICAL DESCRIPTION

Color references are made to The Royal Horticultural Society Colour Chart (R.H.S.) 2001.

TABLE 1

DIFFERENCES BETWEEN THE NEW VARIETY 'VEAZ0038' AND A MOST SIMILAR VARIETY

| | 'VEAZ0038' | 'Empress Royal Purple' |
|---|---|---|
| Flower color: | Deepest velvet purple | Deep Purple |
| Flower, size: | Larger | Smaller |
| Leaf, size: | Medium | Large |
| Plant habit: | Trailing | Semi-upright |

Plant:

*Form, growth and habit*.—Herbaceous, outwardly spreading and trailing, vigorous and free-branching.

*Plant height*.—9.0 cm.

*Plant height* (*inflorescence included*).—13.0 cm.

*Plant width*.—44.0 cm.

Roots:

*Number of days to initiate and produce roots*.—11-13 days at about 23 degrees C.

*Type*.—Fine, fibrous, free branching.

*Color*.—RHS N155B but whiter.

Foliage:

*Arrangement*.—Opposite, simple.

*Immature, leaf color, upper surface*.—RHS 138A.

*Immature, leaf color, lower surface*.—RHS 137C.

*Mature, leaf color, upper surface*.—RHS 137A.

*Mature, leaf color, lower surface*.—RHS 137D.

*Length*.—Approximately 4.0 cm.

*Width*.—3.2-3.4 cm.

*Shape*.—Hastate.

*Base shape*.—Rounded.

*Apex shape*.—Obtuse.

*Margin*.—Dentate.

*Texture, upper surface*.—Pubescent.

*Lower surface*.—Pubescent.

*Color of veins, upper surface*.—RHS 145C.

*Color of veins, lower surface*.—RHS 145D.

*Pattern of veining*.—Pinnate.

*Petiole color*.—RHS 145D.

*Petiole length*.—0.4 cm.

*Petiole width*.—0.3 cm.

*Texture*.—Hirsute.

Stem:

*Branching characteristics*.—Side branches develop potentially at each node.

*Quantity of main branches per plant*.—12 to 18.

*Color of stem*.—RHS 143C.

*Stem length*.—About 17.0-26.0 cm.

*Stem width*.—About 0.32 cm.

*Length of internodes*.—About 2 to 4 cm.

*Texture*.—Hirsute.

*Color of peduncle*.—RHS 138B.

*Length of peduncle*.—From 2.0 to 4.0 cm.

*Peduncle diameter*.—0.2 cm.

*Texture*.—Canescent, also short, transparent glandular hairs.

Inflorescence:

*Type*.—Umbel-like, but actually a spike, umbrella shaped.

*Blooming habit*.—Flowers continuously during the summer months.

*Lastingness of individual blooms on the plant*.—About 6-7 days in the greenhouse.

*Fragrance*.—None.

*Number of inflorescences per plant*.—22 at various stages at development.

*Horizontal diameter of inflorescence*.—5.9-6.7 cm.

*Depth of inflorescence*.—3.2 cm.

*Number of florets and buds per inflorescence*.—Approximately 14-26.

Bud:

*Color*.—RHS N155B.

*Length*.—0.4 cm (future corolla only).

*Width*.—0.3 cm.

*Shape*.—Tubular with bulbous apex.

Floret:

*Form*.—Sessile; salver-shaped, composed of 5 partly fused petals with a base of a narrow tube.

*Immature color, upper surface*.—RHS N92C.

*Immature color, lower surface*.—RHS N92B.

*Mature color, upper surface*.—RHS N92B.

*Mature color, lower surface*.—RHS N92D.

*Floret diameter*.—2.5 cm.

*Floret length* (*depth*).—2.6 cm.

*Petal length*.—1.1 cm.

*Petal width*.—1.3 cm.

*Shape*.—Obcordate.

*Apex shape*.—Emarginate.

*Margin*.—Entire.

*Petal texture, upper surface*.—Papillose; a little glandular hair.

*Petal texture, lower surface*.—Papillose, pubescent.

*Corolla tube length*.—2.0 cm.

*Corolla tube width*.—0.2 cm.

*Corolla tube color inside*.—RHS 155D.

*Tube color outside*.—RHS 93C.

*Corolla texture, inside*.—Pubescent.

*Corolla texture, outside*.—Canescent.

*Throat hair color*.—RHS 155B.

Calyx:

*Type*.—Five sepals whose margins are fused to each other along their length, with a transparent membrane of less than 0.15 cm in width and with one smaller sepal attached to the base of the calyx.

*Color of sepals*.—RHS 143B.

*Length of sepals*.—1.1 cm.

*Width of sepals*.—0.2 cm.

*Sepal shape*.—Fused, linear.

*Apex shape*.—Acute.

*Margins*.—Entire.

*Texture*.—Densely covered with very short glandular hair.

Reproductive organs:

Gynoecium:

*Pistil*.—1.

*Pistil length*.—1.7 cm.

*Style color*.—RHS N144C.

*Style length*.—1.5 cm.

*Stigma color*.—RHS 144A.

*Ovary color*.—RHS 144B.

*Ovary length*.—0.2 cm.

*Ovary width*.—0.1 cm.

Androecium:

*Stamens*.—Anthers and filaments fused to upper half of corolla tube; four anthers with two pollen sacs per anther.

*Color of filaments*.—RHS 151D.

*Filament length*.—0.2 cm.

*Anther color*.—RHS 151D.

*Anther length*.—0.1 cm.

*Pollen amount*.—None observed.

Fertility/seed set: Neither seed nor fruit production has been observed.

Disease/pest resistance: Resistance to pathogens and pests common to *Verbena* has not been observed.

What is claimed is:

1. A new and distinct variety of *Verbena* plant named 'VEAZ0038' substantially as illustrated and described herein.

* * * * *